United States Patent
Lin et al.

(10) Patent No.: US 12,330,972 B2
(45) Date of Patent: Jun. 17, 2025

(54) COMPACT ROTARY ALGAE BIOFILM REACTOR

(71) Applicant: Nanjing University, Nanjing (CN)

(72) Inventors: Yuan Lin, Nanjing (CN); Yueying Liu, Nanjing (CN); Ke Xu, Nanjing (CN); Yuexin Yu, Nanjing (CN); Liye Wang, Nanjing (CN); Yanru Wang, Nanjing (CN); Hongqiang Ren, Nanjing (CN)

(73) Assignee: Nanjing University, Nanjing (CN)

( * ) Notice: Subject to any disclaimer, the term of this patent is extended or adjusted under 35 U.S.C. 154(b) by 0 days.

(21) Appl. No.: 18/804,458

(22) Filed: Aug. 14, 2024

(65) Prior Publication Data
US 2025/0074801 A1    Mar. 6, 2025

(51) Int. Cl.
*C02F 3/32* (2023.01)
*C12M 1/00* (2006.01)
(Continued)

(52) U.S. Cl.
CPC .............. *C02F 3/322* (2013.01); *C12M 21/02* (2013.01); *C12M 23/26* (2013.01); *C12M 27/14* (2013.01);
(Continued)

(58) Field of Classification Search
CPC ... C02F 3/322; C02F 2203/006; C12M 21/02; C12M 23/26; C12M 27/14; G02B 6/262; G02B 6/32
See application file for complete search history.

(56) References Cited

U.S. PATENT DOCUMENTS

| | | | | |
|---|---|---|---|---|
| 4,555,864 A | * | 12/1985 | Mori | ...................... C12M 31/04 |
| | | | | 126/685 |
| 4,902,089 A | * | 2/1990 | Mori | ...................... F24S 23/31 |
| | | | | 385/33 |

(Continued)

FOREIGN PATENT DOCUMENTS

| CN | 1796268 A | 7/2006 |
|---|---|---|
| CN | 2017111906507 | 4/2018 |

(Continued)

OTHER PUBLICATIONS

Search Report, issued in CN202311103309.9 (priority application), by CNIPA, dated Apr. 17, 2024.

(Continued)

*Primary Examiner* — William H. Beisner
*Assistant Examiner* — Danielle B Henkel
(74) *Attorney, Agent, or Firm* — Zhu Lehnhoff LLP

(57) ABSTRACT

A compact rotary algae biofilm reactor includes an algae biofilm module and a light guide module. The algae biofilm module includes a plurality of rotary members and a reaction tank. In the rotary member, an algae biofilm growth carrier and a power transmission belt are wound on a driving shaft and a driven shaft. A top end of the rotary member is fixed on a fixing frame while a bottom end thereof is submerged in the reaction tank. The light guide module includes a rotatable lens holder. The rotatable lens holder is fixedly provided with a linear Fresnel lens on an upper end thereof and is provided with a light guide plate on a lower end thereof. One side of the linear Fresnel lens is provided with a step motor configured to control the linear Fresnel lens to rotate with an angle of sunlight.

16 Claims, 14 Drawing Sheets

(51) Int. Cl.
   *C12M 3/06* (2006.01)
   *G02B 6/26* (2006.01)
   *G02B 6/32* (2006.01)
(52) U.S. Cl.
   CPC .............. *G02B 6/262* (2013.01); *G02B 6/32* (2013.01); *C02F 2203/006* (2013.01)

(56) References Cited

U.S. PATENT DOCUMENTS

| | | | | |
|---|---|---|---|---|
| 5,162,051 | A * | 11/1992 | Hoeksema | C12M 31/10 422/186 |
| 6,287,852 | B1 * | 9/2001 | Kondo | C12M 21/02 47/1.4 |
| 6,603,069 | B1 * | 8/2003 | Muhs | F21S 19/005 136/246 |
| 7,824,904 | B1 * | 11/2010 | Dimanshteyn | C12M 31/12 362/101 |
| 2003/0073231 | A1 * | 4/2003 | Dutil | C12M 39/00 47/1.4 |
| 2007/0264708 | A1 * | 11/2007 | Bayless | C12M 31/08 435/257.1 |
| 2008/0220515 | A1 * | 9/2008 | McCall | C12M 21/02 47/1.4 |
| 2009/0023199 | A1 * | 1/2009 | Gal | C12M 31/08 435/293.1 |
| 2010/0105125 | A1 * | 4/2010 | Haley, III | C12M 43/04 435/257.1 |
| 2011/0070632 | A1 * | 3/2011 | Katoch | C12M 39/00 15/4 |
| 2013/0337548 | A1 * | 12/2013 | Sims | C12M 27/10 435/257.1 |
| 2014/0127776 | A1 * | 5/2014 | Picard | C12M 23/48 435/178 |
| 2014/0273174 | A1 * | 9/2014 | Gross | C12M 27/14 435/257.1 |
| 2015/0370054 | A1 * | 12/2015 | Becker | G02B 6/262 250/206 |
| 2016/0130547 | A1 * | 5/2016 | Venkataramu | C12M 27/22 435/286.7 |
| 2016/0152933 | A1 * | 6/2016 | Bernard | C12M 23/48 435/257.1 |
| 2020/0048122 | A1 * | 2/2020 | Gross | C02F 3/322 |
| 2020/0231477 | A1 * | 7/2020 | Wen | C02F 3/08 |
| 2021/0024861 | A1 * | 1/2021 | He | C12M 47/18 |

FOREIGN PATENT DOCUMENTS

| | | |
|---|---|---|
| CN | 208151054 U | 11/2018 |
| CN | 108954865 A | 12/2018 |
| CN | 111363676 A | 7/2020 |
| CN | 111763604 A | 10/2020 |
| CN | 113354211 A | 9/2021 |
| CN | 114394672 A | 4/2022 |
| CN | 108163972 B | 4/2023 |

OTHER PUBLICATIONS

Search Report, prepared by Beijing Zhanqiao Intellectual Property Agency, dated Jul. 17, 2024.
Notice of Grant of Patent Rights, issued in CN202311103309.9 (priority application), by CNIPA, dated Jun. 4, 2024.

* cited by examiner

COMPACT ROTARY ALGAE BIOFILM REACTOR

REFERENCE TO RELATED APPLICATIONS

The present application claims the priority of Chinese patent application No. 202311103309.9, filed on 2023 Aug. 30, the entire disclosure of which is incorporated herein by reference.

TECHNICAL FIELD

The present disclosure relates to a compact rotary algae biofilm reactor, belonging to the technical field of sewage treatment.

BACKGROUND

Currently, the mainstream sewage treatment process is centered around activated sludge methods, which have problems of high energy and chemical consumption and are contrary to the development direction of low-carbon transformation in the sewage treatment industry. In recent years, microalgae-based sewage treatment technology has attracted widespread attention due to its advantages in efficiently removing pollutants (nitrogen, phosphorus, heavy metals, chemicals, etc.), fixing $CO_2$, and producing biofuels, and has broad application prospects. The use of algae biofilm further breaks through the problem of difficulty in biomass harvesting in suspended microalgae treatment technologies. However, the current algae biofilm technology still has problems of low substance content, resulting in low load per unit area. Therefore, it is imperative to develop more efficient compact algal biofilm reactors.

CN108163972A discloses an algae rotary biofilm reactor system based on dephosphorization and denitrification and an application thereof. Specifically, a flexible carrier with an algae biofilm formed in advance is fixed on a conveyor belt style rotatable device, and the rotating device is placed above an activated sludge tank. A bottom of a rotating element contacts sewage and activated sludge, forming a coupling relationship with the activated sludge to remove organic matters, nitrogen, phosphorus and other substances in the sewage. On the other hand, an upper end of the rotating element is exposed to sunlight and air, allowing algae to produce oxygen and grow through photosynthesis. The above method has the following problems. (1) A large distance needs to be reserved between vertically placed rotating members in the algae biofilm system to avoid mutual shielding. However, the fact to ensure that the algae biofilm on each rotating member can receive sufficient light illumination limits the amount of algae biofilm per unit area, indirectly increasing the footprint of the device. (2) The angle of sunlight illumination changes with time, which is prone to non-uniform illumination to result in unstable treatment effects. On one hand, when the angle of sunlight incidence is large (in the morning and evening), the films tend to shield each other. On the other hand, when the angle of sunlight incidence is small, a large amount of sunlight directly irradiates on the gap between the rotating members, resulting in a low utilization of sunlight. (3) Coupling the algal biofilm and the activated sludge together still requires aeration that consumes a lot of energy, failing to fully utilize the synergistic advantages of the algal biofilm in reducing pollution and carbon dioxide. In addition, the aeration can easily cause the algal biofilm to fall off. Furthermore, the activated sludge easily adheres onto the algae biofilm during the contact process, which is not conducive to the photosynthesis of the algae biofilm.

Some inventions employ light guide plates to increase the illumination inside the reactors in order to increase the growth amount of the algae biofilm. For example, CN111647501A discloses a multi-layer stacked adsorption microalgae biofilm photobioreactor based on a light guide carrier. The reactor is composed of multiple layers of stacked solid light guide plates, and an LED light strip is installed on a left side of each layer of solid light guide plate. The light guide plate serves as a light source transmission, conversion medium and an adsorption microalgae biofilm carrier to achieve multi-layer stacked culturing of microalgae cells, thereby increasing the microalgae biomass yield per unit area. In addition, CN112852588A discloses a light-guide three-dimensional porous biofilm substrate reactor and a method for culturing a microalgae biofilm. Specifically, a light-guide biofilm carrier with a three-dimensional porous structure is placed in the main body of the reactor. Each layer of light-guide biofilm is embedded with side light-guide optical fibers and is connected to a dedicated optical fiber light source through an optical fiber collector. There are also light-guide nanoparticles uniformly added in the light-guide biofilms. The light-guide nanoparticles uniformly scatter the light received by the side light-guide fiber around. However, these methods are limited by the fact that the light guide plate needs to be fixed and the light incident end is narrow, so they cannot effectively utilize the sunlight with constantly changing angles. Therefore, only fixed artificial light sources (such as LED light strips and optical fibers, etc.) can be used, which undoubtedly increases operating costs and does not conform to the concept of low carbon.

SUMMARY

Purpose of Invention: it is an object of the present disclosure to provide a compact rotary algae biofilm reactor, which is equipped with a light guide module to improve the utilization rate of sunlight, allows vertically rotated algae biofilm carriers to be arranged closer, needs no activated sludge system, and can significantly improve the amount of biomass per unit area, whereby improves the efficiencies of sewage treatment and algae production and achieves the high-efficiency low carbon treatment of sewage.

Technical Solution: a compact rotary algae biofilm reactor according to the present disclosure is composed an algae biofilm module and a light guide module embedded therein, wherein the algae biofilm module includes a plurality of rotary members and a reaction tank, the reaction tank is provided with a fixing frame on an upper part thereof, and the rotary member includes a low-speed motor, an algae biofilm growth carrier and a power transmission belt. The low-speed motor is fixed on an upper part of the fixing frame, one side of the low-speed motor is connected with a driving shaft, the reaction tank is provided with a driven shaft below a liquid surface therein, and the algae biofilm growth carrier and the power transmission belt are wound on the driving shaft and the driven shaft. The light guide module includes a rotatable lens holder, the rotatable lens holder is fixedly provided with a linear Fresnel lens on an upper end thereof, the rotatable lens holder is provided with a light guide plate on a lower end thereof, one side of the linear Fresnel lens is provided with a step motor, and the step motor is arranged on the fixing frame.

Further, the number of the rotary members is two or more.

Further, the linear Fresnel lens can be driven by the step motor to slowly rotate with a change of angle of sunlight, so that the sunlight is always linearly focused on one side of the light guide plate to form an area light source on the light guide plate, and the light guide plate is fixed between and parallel to adjacent rotary members.

Furthermore, the linear Fresnel lens is arranged on a top end of two adjacent rotary members, the light guide plate is vertically inserted between adjacent rotary members and is parallel to a surface of the algae biofilm growth carrier.

Further, the rotatable lens holder has a base in an inverted V shape.

Further, the algae biofilm growth carrier is a flexible material.

Furthermore, the flexible material is a silicone film, nylon cloth, a cotton and linen product or a flexible plastic.

Further, the low-speed motor is connected to the driving shaft and rotated, and the power transmission belt drives the driven shaft submerged under the liquid surface of the reaction tank to rotate, so that the algae biofilm growth carrier is rotated alternately in the gas-liquid medium following the power transmission belt.

Further, the step motor and the low-speed motor can be arranged on a same side or different sides of the fixing frame.

Further, a water inlet is provided at a bottom of one side of the reaction tank, and a water outlet is provided on another side opposite the water inlet.

Beneficial Effects: compared with the conventional art, the present disclosure has the following significant benefits.

(1) The present disclosure can arrange more rotary members with the same floor area and vertical space, by redirecting light illumination and making full use of an inside space of the algae biofilm reactor, thereby significantly improving biomass and being conducive to improving the efficiency of treatment.

(2) The present disclosure improves the utilization rate of sunlight, reduces the problem of non-uniform light illumination due to a change of angle of sunlight incidence and adjacent algae biofilms shielding each other, and is conducive to improving the stability of the reactor.

(3) The biosystem of the present disclosure is simple in composition, avoids sludge adhering onto the biofilms to result in shielding and needs no extra aeration device, whereby reduces the risk of algae biofilms falling off due to aeration, and meanwhile saves the power consumption caused by extra aeration and enhances economic efficiency.

DETAILED DESCRIPTION OF THE EMBODIMENTS

The technical solution of the present disclosure is further illustrated below in conjunction with the drawings.

Figure 1:
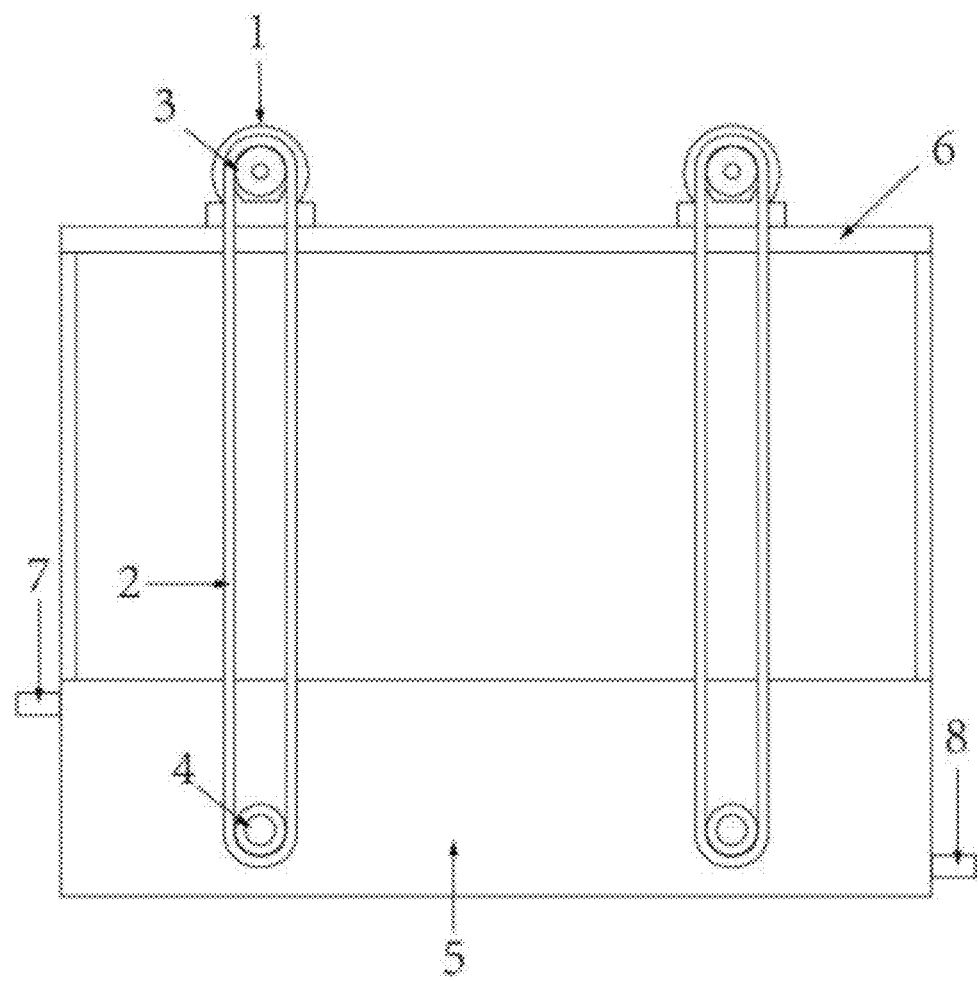
FIG. 1 is a front view of an algae biofilm module in a compact rotary algae biofilm reactor of the present disclosure.
Figure 2:
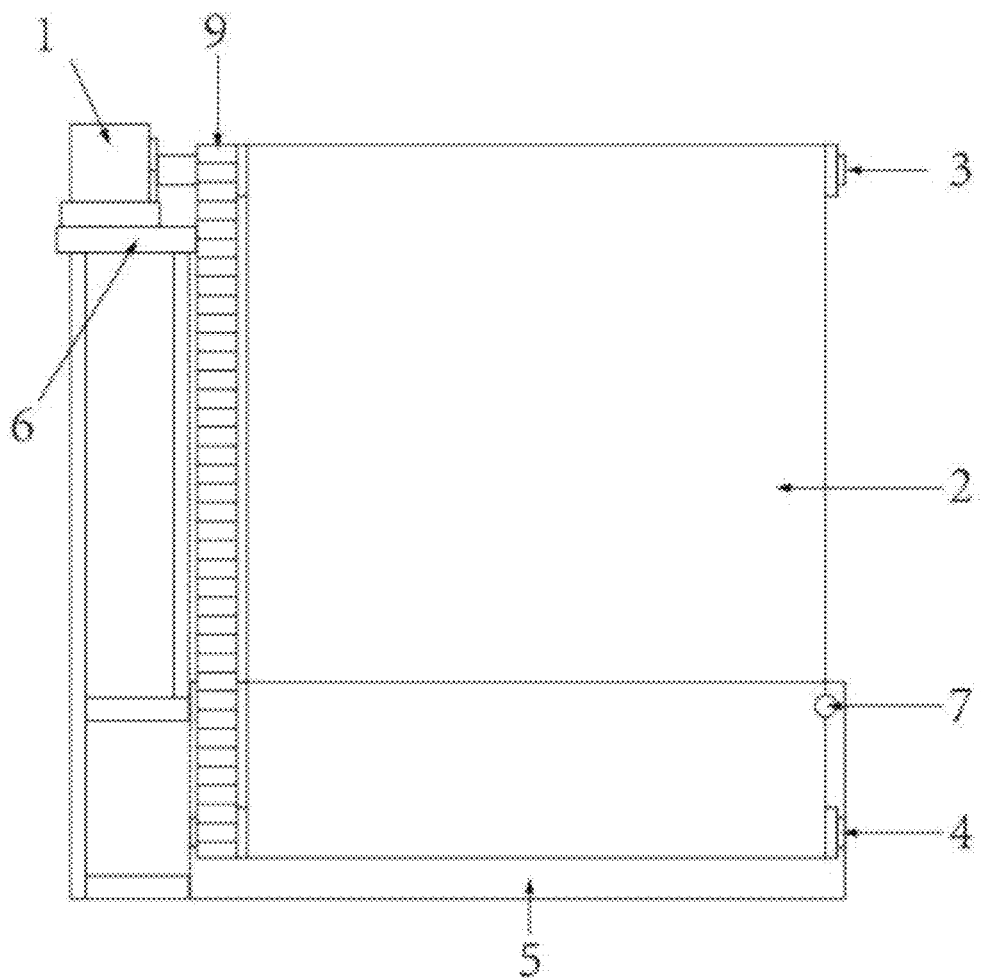
FIG. 2 is a left view of an algae biofilm module in a compact rotary algae biofilm reactor of the present disclosure.
Figure 3:
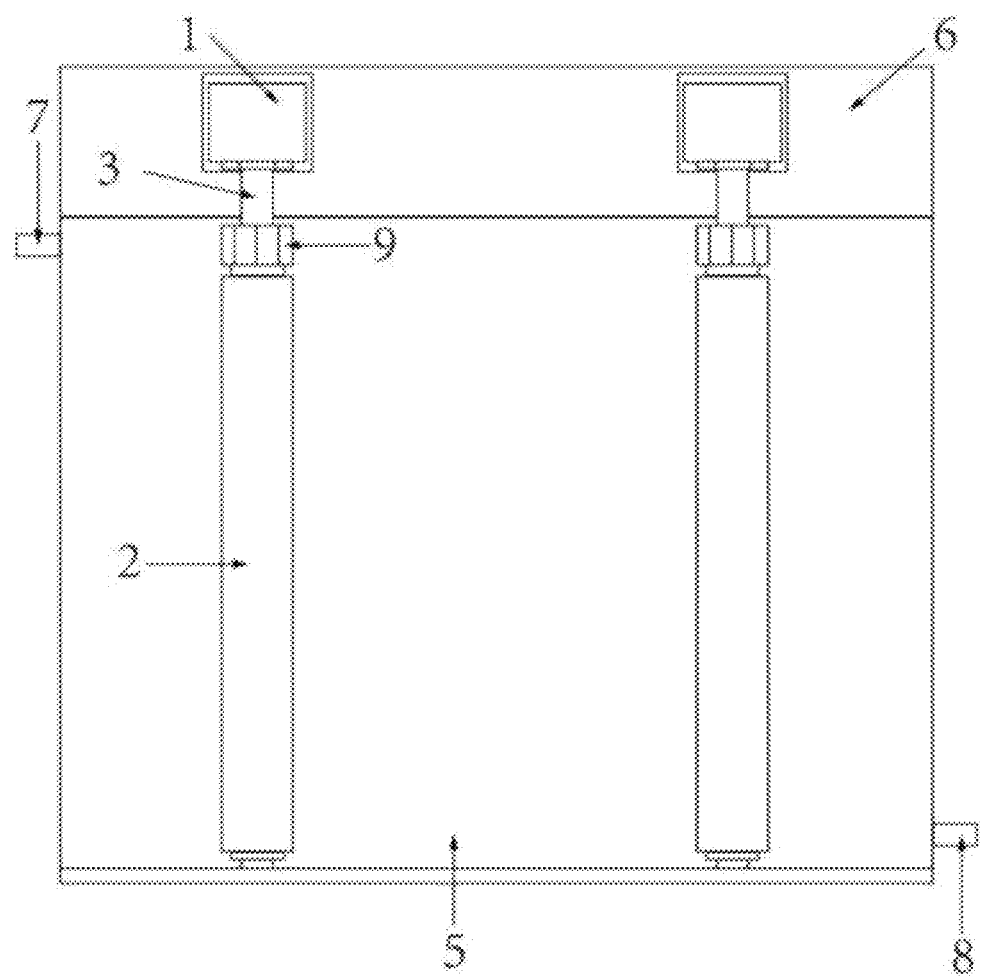
FIG. 3 is a top view of an algae biofilm module in a compact rotary algae biofilm reactor of the present disclosure.

A compact rotary algae biofilm reactor according to the present disclosure, as shown in FIG. 1 to FIG. 6, is composed of an algae biofilm module and a light guide module embedded therein, wherein as shown in FIG. 1 to FIG. 3 the algae biofilm module includes a plurality of rotary members and a reaction tank 5 (for example, there may be 2 rotary members, as shown in FIG. 2). The reaction tank 5 is provided with a fixing frame 6 on an upper part thereof. The rotary member includes a low-speed motor 1, an algae biofilm growth carrier 2, a driving shaft 3, a driven shaft 4 and a power transmission belt 9. The low-speed motor 1 is fixed on an upper part of the fixing frame 6. One side of the low-speed motor 1 is connected with the driving shaft 3. The driven shaft 4 is arranged below a liquid surface in the reaction tank 5, vertical to the driving shaft 3. The algae biofilm growth carrier 2 and the power transmission belt 9 are wound on the driving shaft 3 and the driven shaft 4. A water inlet 8 is provided at a bottom of one side of the reaction tank 5, and a water outlet 7 is provided on another side opposite the water inlet 8.

The algae biofilm growth carrier 2 is a flexible material such as a silicone film, nylon cloth, a cotton and linen product or a flexible plastic, etc. The low-speed motor 1 with speed regulation function is connected to the driving shaft 3 and rotated, and the power transmission belt 9 drives the driven shaft 4 submerged under the liquid surface of the reaction tank 5 to rotate, so that the loaded algae biofilm growth carrier is rotated alternately in a gas-liquid medium following the power transmission belt 9.

A plurality of rotary members perpendicular to the ground and arranged in parallel form a main body part of the algae biofilm module together with the reaction tank 5. The fixing frame 6 is configured to place the low-speed motor 1 and keep the stability of the overall structure of the compact rotary algae biofilm reactor. The reaction tank 5 is infused with sewage via the bottom water inlet 8 and drains treated water via the upper water outlet 7 on another side. It is to be noted that the rotary members have a big distance therebetween in FIG. 1 to FIG. 3 for an illustrative purpose. In practical applications, the distance between adjacent rotary members should be dynamically adjusted depending on actual needs, to make full use of the light scattered by the light guide plate.

Figure 4:
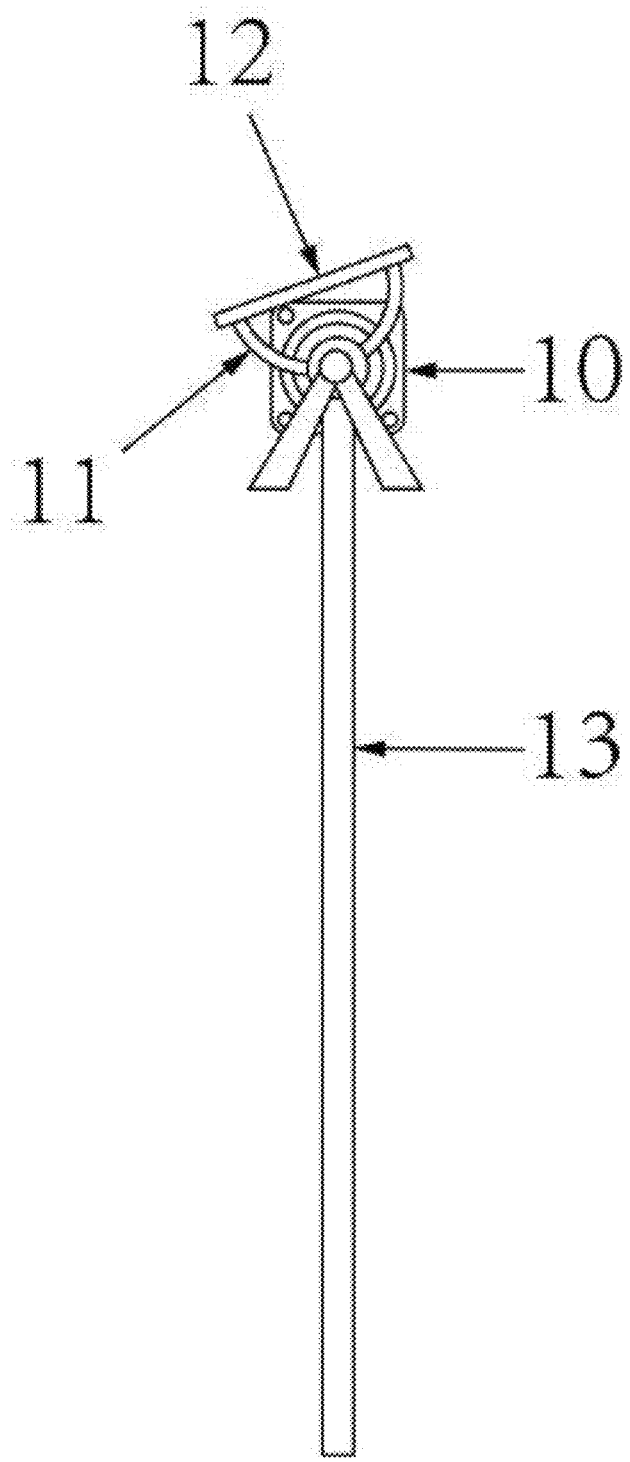
FIG. 4 is a front view of a light guide module in a compact rotary algae biofilm reactor of the present disclosure.
Figure 5:
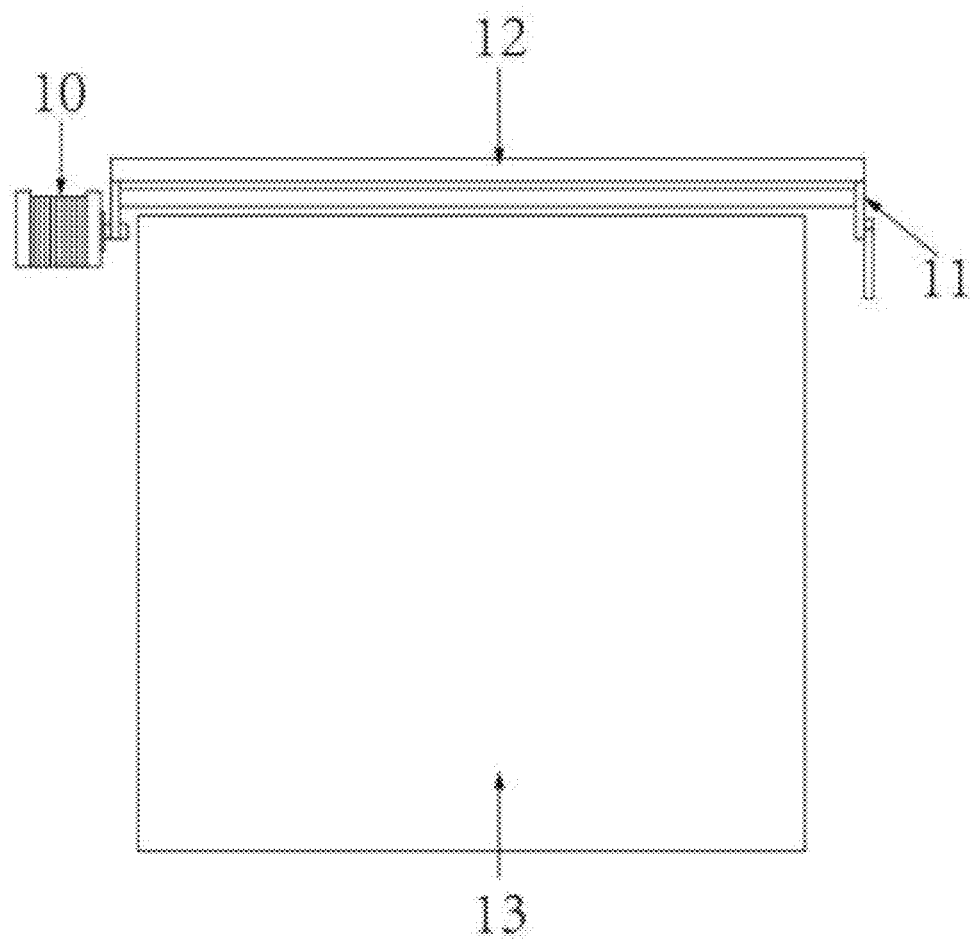
FIG. 5 is a left view of a light guide module in a compact rotary algae biofilm reactor of the present disclosure.
Figure 6:
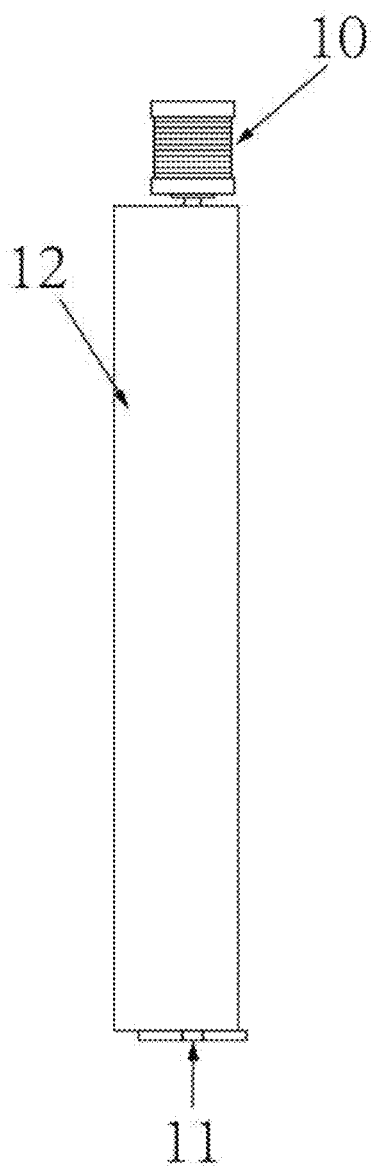
FIG. 6 is a top view of a light guide module in a compact rotary algae biofilm reactor of the present disclosure.
Figure 7:
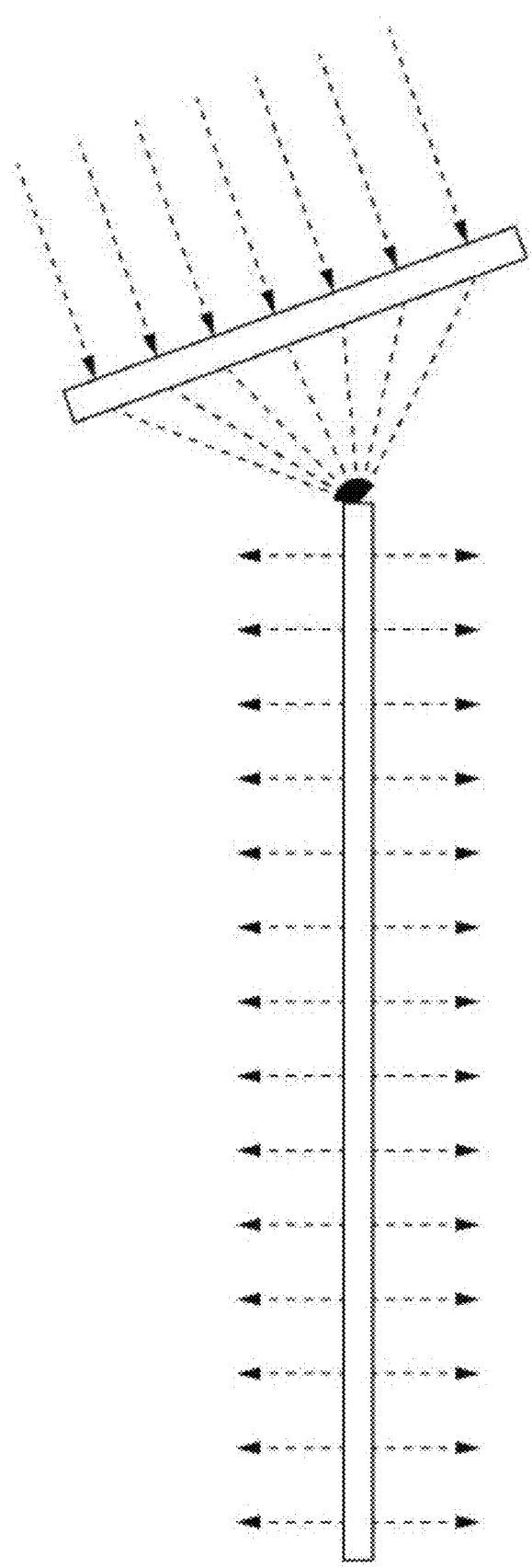
FIG. 7 is a schematic diagram of a light guide module in a compact rotary algae biofilm reactor of the present disclosure.

As shown in FIG. 4 to FIG. 6, the light guide module includes a step motor 10, a rotatable lens holder 11, a linear Fresnel lens 12 and a light guide plate 13. The linear Fresnel lens 12 is fixed on the rotatable lens holder 11. The rotatable lens holder 11 has a base in an inverted V shape. The light guide plate 13 is arranged on a lower end of the inverted V shaped base. One side of the linear Fresnel lens 12 is provided with the step motor 10. Sunlight is focused into a linear narrow light band by the linear Fresnel lens 12. The linear Fresnel lens 12 is driven by the step motor 10 to slowly rotate with a change of angle of sunlight, so that the sunlight is always linearly focused on one side of the light guide plate 13 to form an area light source on the light guide plate 13 (the light path principle is as shown in FIG. 7). The light guide plate 13 is fixed between and parallel to adjacent algae biofilm rotary members, to provide uniform and stable light illumination for algae biofilms on two sides thereof.

Figure 8:
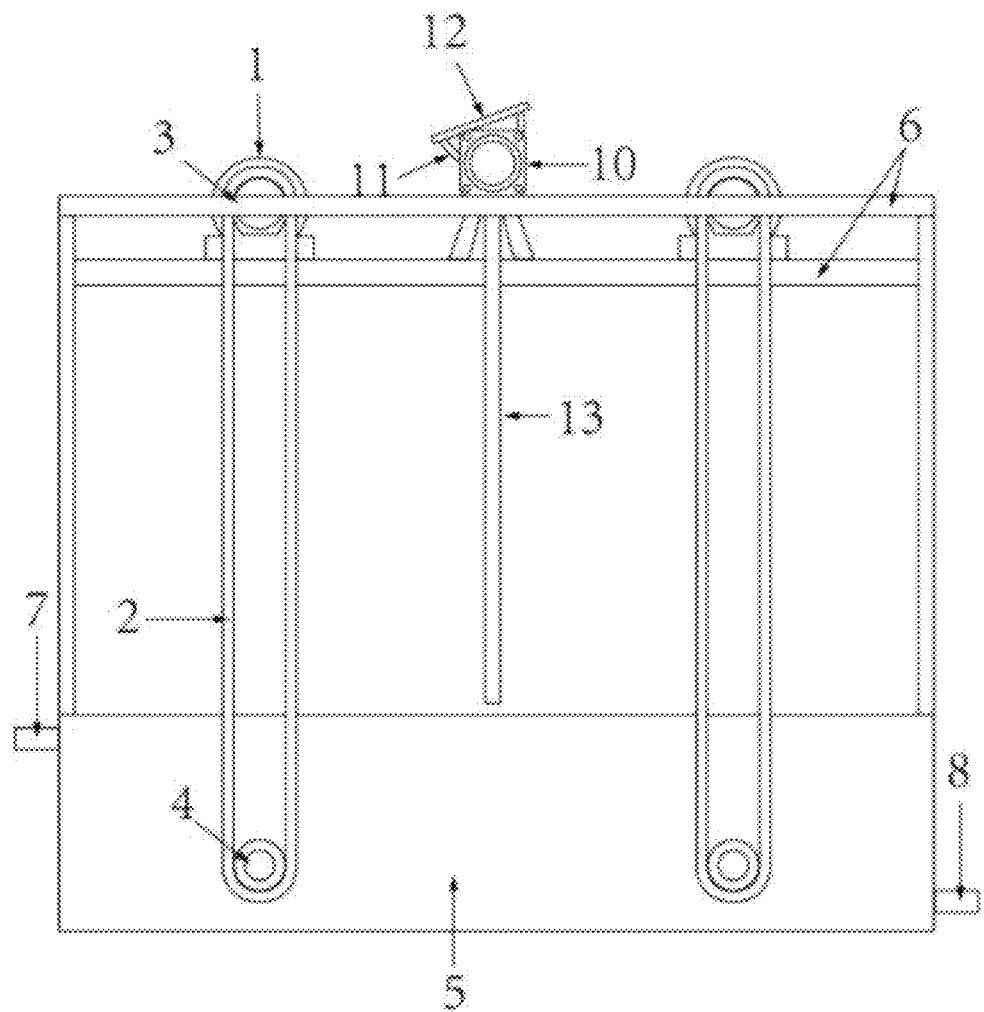
FIG. 8 is a front view of a compact rotary algae biofilm reactor of the present disclosure.
Figure 9:
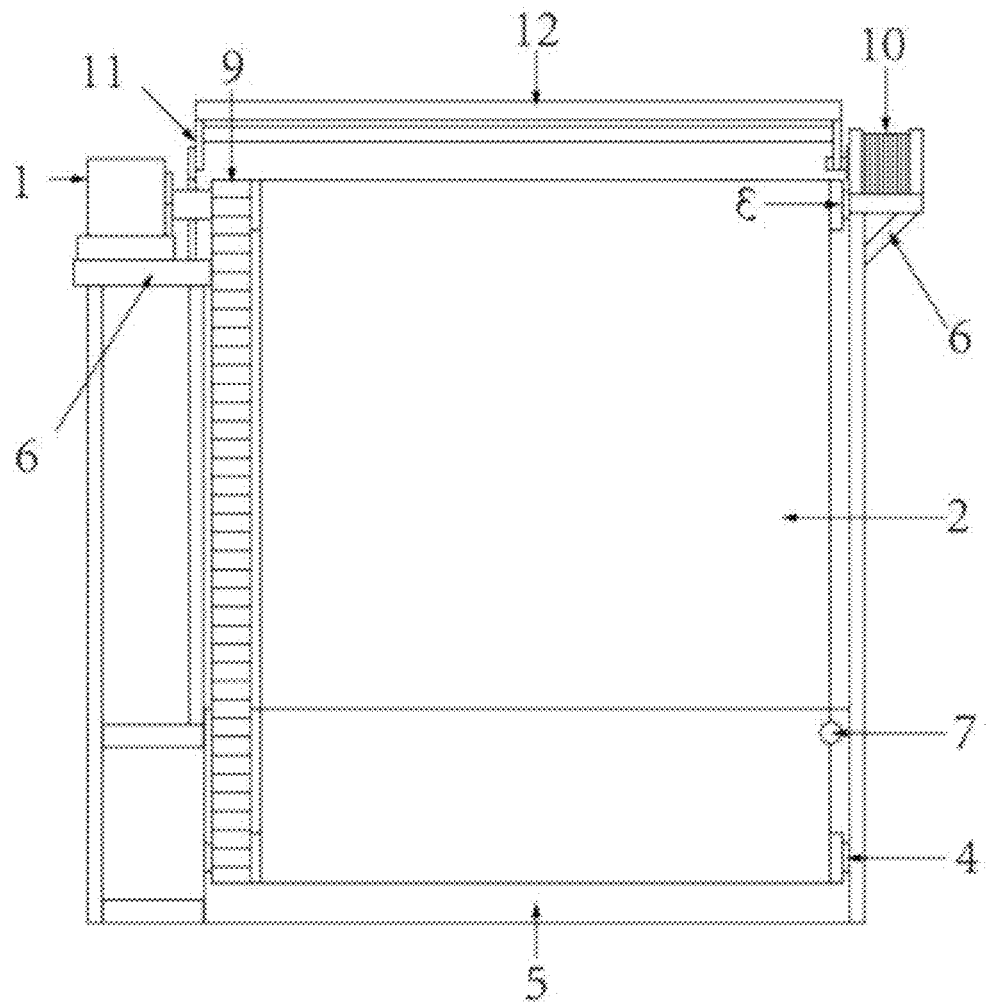
FIG. 9 is a left view of a compact rotary algae biofilm reactor of the present disclosure.
Figure 10:
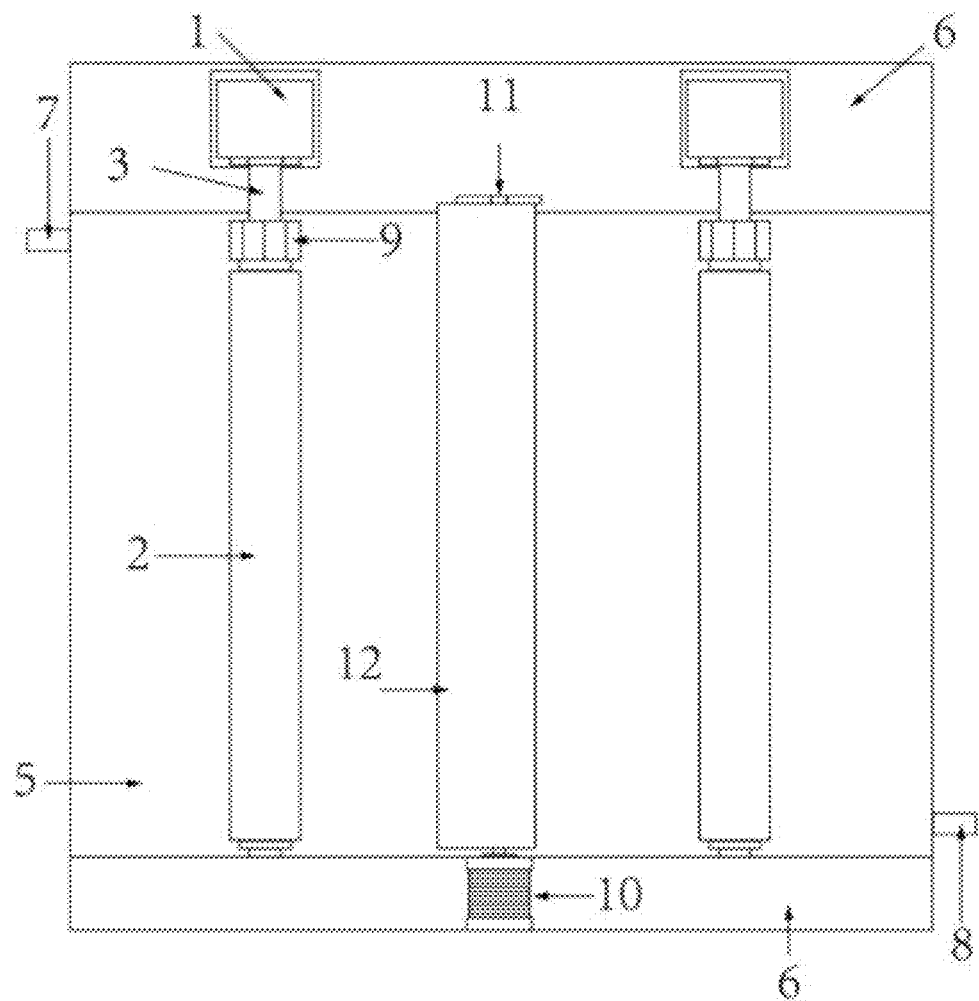
FIG. 10 is a top view of a compact rotary algae biofilm reactor of the present disclosure.

A plurality of light guide modules (which equals to the number of rotary members minus 1) are arranged in the algae biofilm reactor, so that the linear Fresnel lens 12 is located on a top end of two adjacent rotary members, and the light guide plate 13 is vertically inserted between two rotary members and parallel to the surface of the algae biofilm growth carrier 2. The step motor 10 is arranged on the fixing frame. For convenient illustration, the step motor 10 and the low-speed motor 1 are arranged on two sides of the fixing frame 6 of the algae biofilm reactor respectively in FIG. 10. In practical conditions, the step motor 10 and the low-speed motor 1 can be arranged on a same side or different sides depending on sizes and placement spaces. To sum up, the above forms the compact rotary algae biofilm reactor of the present disclosure (as shown in FIG. 8 to FIG. 10).

Embodiment 1

Figure 11:
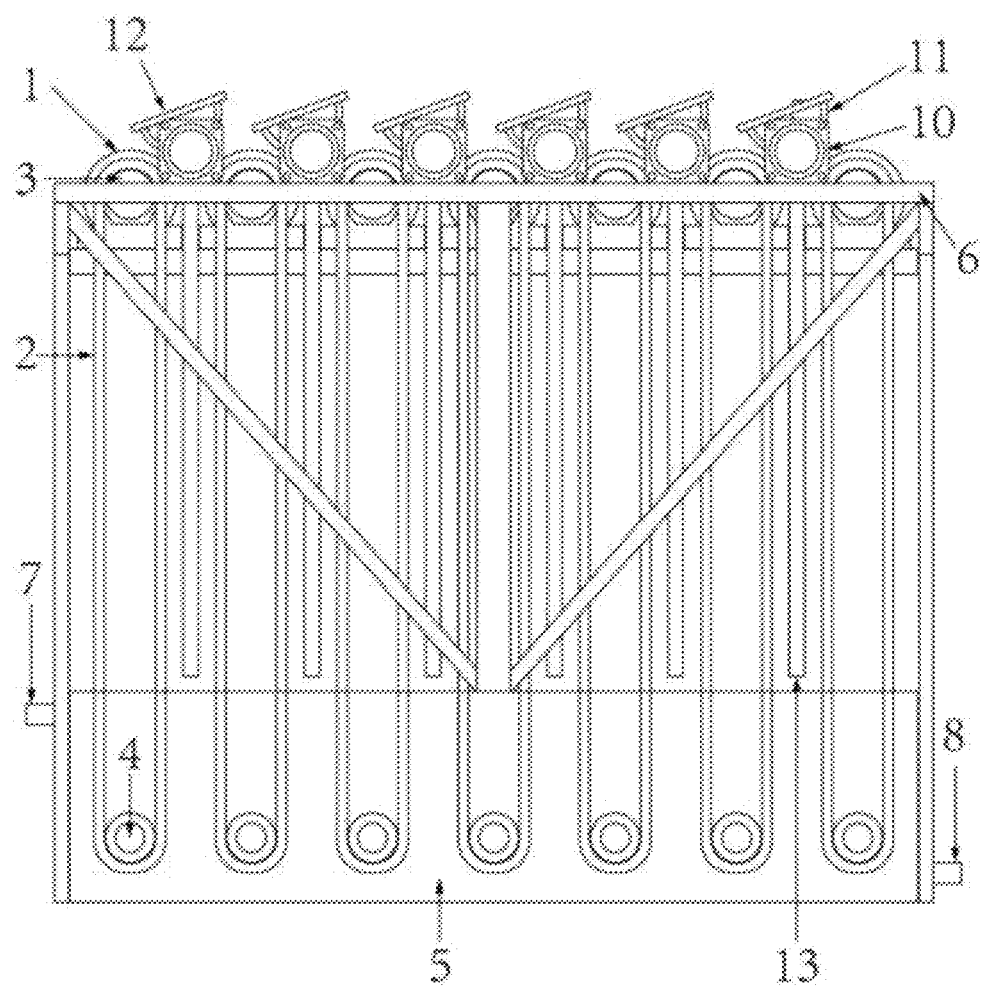
FIG. 11 is a front view of a compact rotary algae biofilm reactor illustrated in Embodiment 1.
Figure 12:
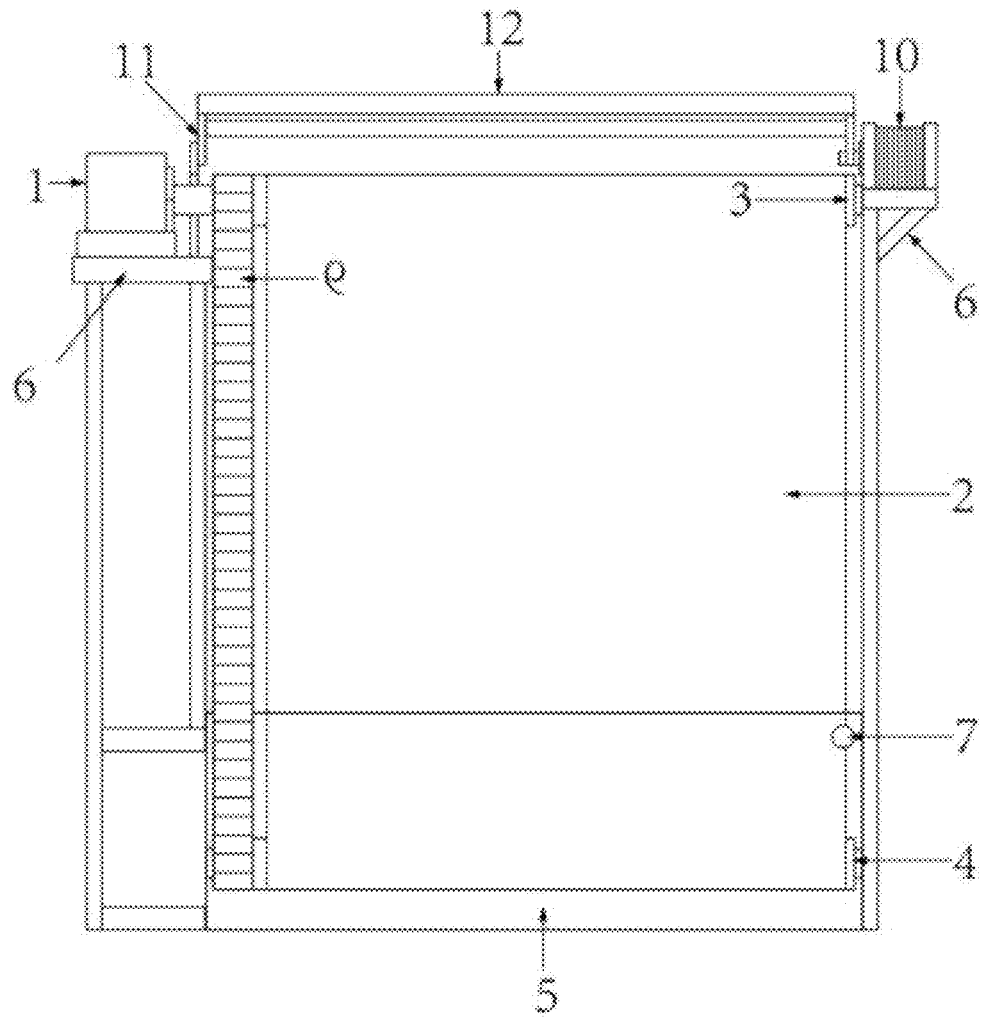
FIG. 12 is a left view of a compact rotary algae biofilm reactor illustrated in Embodiment 1.
Figure 13:
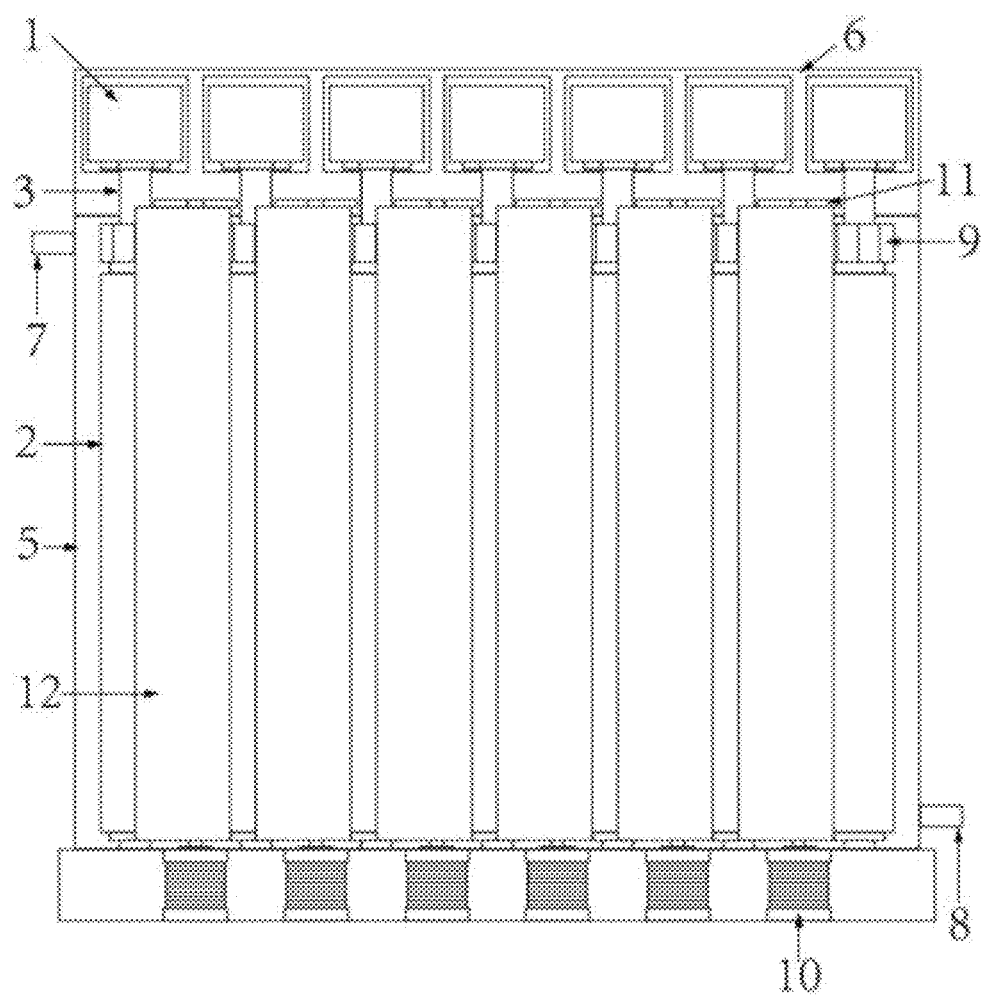
FIG. 13 is a top view of a compact rotary algae biofilm reactor illustrated in Embodiment 1.

A compact algae biofilm reactor has been set up according to the form described above that contains an algae biofilm module with seven rotary members and contains six sets of light guide modules. As shown in FIG. 11 to FIG. 13, one end of a driving shaft 3 is connected to a low-speed motor 1 in a manner of coupling connection, flange connection and coaxial connection, while another end thereof is connected to a bearing on a fixing frame 6. The low-speed motor 1 is equipped with an electronic control module capable of adjusting a rotation rate used for driving the driving shaft 3, the rotation rate being 1 RPM to 300 RPM. The driving shaft 3 and a driven shaft 4 are connected through gears and a power transmission belt 9 with teeth, where the driving shaft 3 is above while the driven shaft 4 is below. When the driving shaft 3 is rotating, the driven shaft 4 is driven to move synchronously by means of a force transmission function of the power transmission belt 9. A flexible algae biofilm growth carrier 2 are wound on the driving shaft 3 and the driven shaft 4 to rotate in the form of transmission belt. The rotary member and a reaction tank 5 form the algae biofilm module. During actual operation, the bottom of the rotary member is submerged below a liquid surface of the reaction tank 5, and two ends of the driven shaft 4 are fixed below the liquid surface of the reaction tank 5 by means of bearings. When the flexible algae biofilm growth carrier 2 is rotated in the form of transmission belt, an algae biofilm loaded on the flexible algae biofilm growth carrier 2 circulates at the gas-liquid interface. A water outlet 7 is arranged at the liquid surface of the reaction tank 5, and a water inlet 8 is arranged at a wall bottom of the reaction tank 5 on an opposite side of the water outlet 7. A bottom base of the fixing frame 6 is connected to the reaction tank 5. Two bearing platforms on the fixing frame 6 are located on two sides of an upper part of the reaction tank 5 respectively, for installing the rotary members and the light guide module. A step motor 10 is connected to one end of a bottom rotating shaft of a rotatable lens holder 11, while another end thereof is connected to a bearing on an inverted V shaped bracket base. The step motor 10 is inbuilt with a programmable system to accurately control the rotation of the rotatable lens holder 11, so that a plane of a linear Fresnel lens 12 always keeps perpendicular to incident sunlight. A light guide plate 13 has two sides of a top end thereof fixed on the fixing frame 6, vertically hanging in a gap between adjacent algae biofilm rotary members and parallel to the plane of the algae biofilm. A focus point where the linear Fresnel lens 12 converges sunlight is an incident end of the light guide plate 13, and the converged incident light is uniformly scattered by the light guide plate 13 to provide a stable light illumination for the algae biofilm on two sides thereof. In the present embodiment, the six sets of light guide modules 6 are distributed in the gaps of the seven rotary members respectively.

From the above, in the conditions of a same floor area and a same vertical height of algae biofilm, the compact rotary algae biofilm reactor according to the present disclosure can be equipped with 2 to 3 times of the number of the rotary members compared to the conventional rotary algae biofilm reactors, which greatly improves the utilization rate of ground and the volumetric load of the reactor, thereby reduces the cost of the algae biofilm treating sewage and improves the efficiency of treatment.

Embodiment 2

The algae biofilm reactor illustrated in Embodiment 1 was employed to perform sewage treatment, including the steps as follows.

1. Algal biofilm communities were acquired from a secondary sedimentation tank wall of an actual sewage treatment plant, and then were inoculated onto the algae biofilm growth carrier 2 and submerged into a synthetic wastewater simulating a typical municipal sewage quality (with wastewater COD 180 mg/L, total nitrogen 40 mg/L, total phosphorus 3.5 mg/L) to form a biofilm.

3. The flexible algae biofilm growth carrier 2 with the biofilm formed was attached on the driving shaft 3 and the driven shaft 4 of the rotary member. The algae biofilm reactor ran in a sequence batch mode, where the treated water was drained from the water outlet 7 at 6 am every day and the newly configured synthetic wastewater was infused from the water inlet 8. The corresponding hydraulic retention time was 24 h, and a harvest interval of 20$d$ was set.

Figure 14:
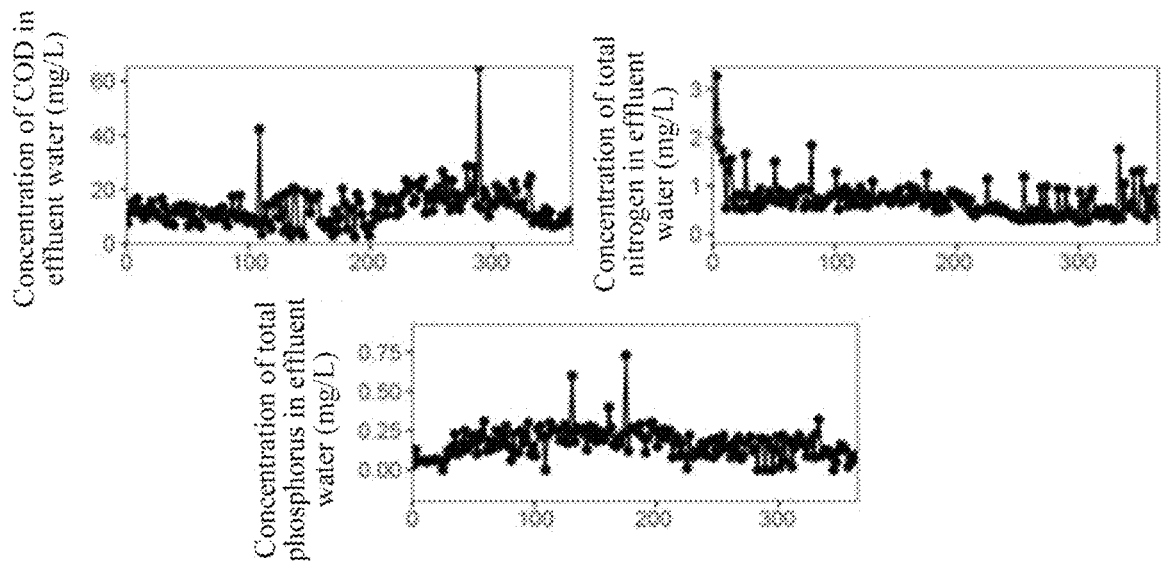
FIG. 14 is a diagram showing an effect of sewage treatment by a compact rotary algae biofilm reactor illustrated in Embodiment 2.

3. A potassium dichromate method (HJ 828-2017), an alkaline potassium persulphate digestion-UV spectrophotometric method (HJ 636-2017), and an ammonium molybdate spectrophotometry (GB 11893-1989) were employed to measure concentrations of the COD, the total nitrogen and the total phosphorus in water samples respectively, where the sampling interval was once every two days and the running time lasted one year. The results are as shown in FIG. 14. From FIG. 14, with the present method treating the typical municipal sewage, the effluent water can have the COD stably less than 30 mg/L, the total nitrogen stably less than 2 mg/L and the total phosphorus stably less than 0.5, which meets the Class-I A standard limit regulated in the «Pollutant Discharge Standards for Municipal Wastewater Treatment Plants» GB18918-2002.

CONTRAST EXAMPLE 1

Figure 15:
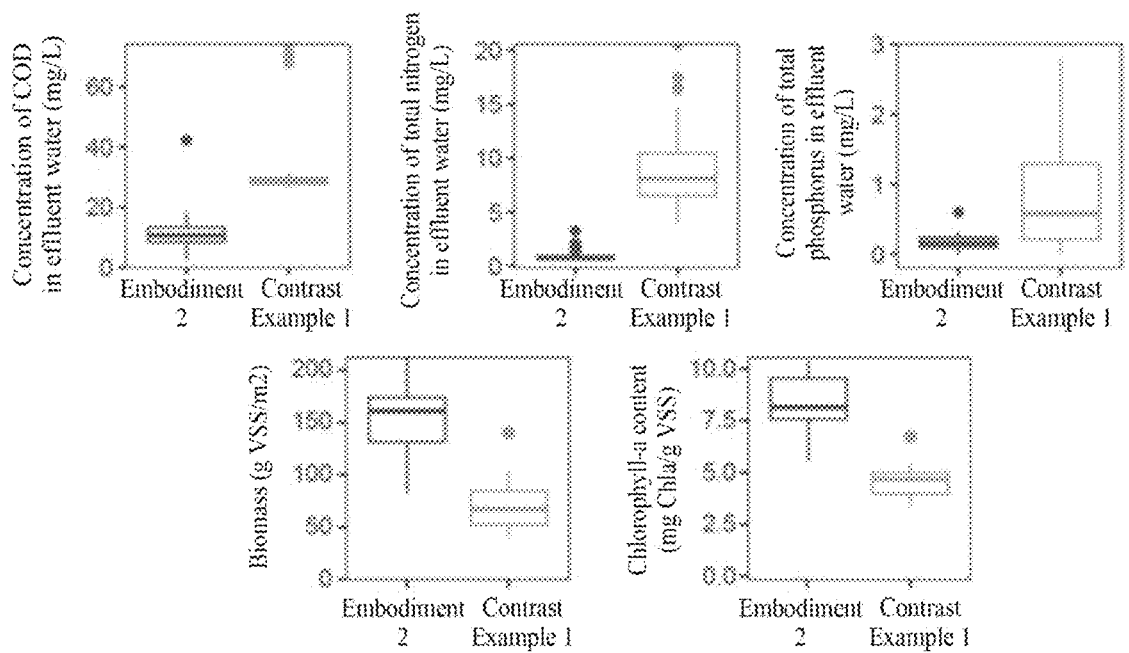
FIG. 15 is a diagram showing changes in sewage treatment efficiency and algae biofilm growth of an algae biofilm reactor with a light guide module removed illustrated in Embodiment 3.

The algae biofilm reactor only had the light guide module removed compared to Embodiment 1, where the experimental steps were the same as in Embodiment 2. It is contrasted with Embodiment 2 to learn changes in sewage treatment effect and algae biofilm growth of the reactor with the light guide module removed. The algae biofilm growth condition was expressed in terms of biomass per unit area (g VSS/m2) and chlorophyll-a content (mg Chla/g VSS). The biomass was measured by a weighing method. The chlorophyll-a content was measured by a spectrophotometric method. The results are as shown in FIG. 15. From FIG. 15, when the light guide module is removed in the Contrast Example 1, the effluent water of the reactor has concentrations of the COD, the total nitrogen and the total phosphorus all increased, while the biomass per unit area and the chlorophyll-a content are obviously reduced. The above result indicates that after the light guide module is removed, the light illumination is not uniform, leading to inhibition of the biomass accumulation and the algae growth of the algae biofilm, thus inhibiting the sewage treatment efficiency of the reactor. Therefore, excellent processing effects of the compact reactor can only be achieved by combining the light guide module of the present disclosure with the reactor.

The invention claimed is:

1. A compact rotary algae biofilm reactor comprising an algae biofilm module and a light guide module embedded therein, wherein the algae biofilm module comprises a plurality of rotary members and a reaction tank (5) containing no activated sludge, the reaction tank (5) is provided with a fixing frame (6) on an upper part thereof, and the rotary member comprises a low-speed motor (1), an algae biofilm growth carrier (2) and a power transmission belt (9), wherein the low-speed motor (1) is fixed on an upper part of the fixing frame (6), one side of the low-speed motor (1) is connected with a driving shaft (3), the reaction tank (5) is provided with a driven shaft (4) below a liquid surface therein, above the liquid surface of the reaction tank (5) is air and below is a liquid, the air and the liquid form a gas-liquid medium, and the algae biofilm growth carrier (2) and the power transmission belt (9) are both wound on the driving shaft (3) and the driven shaft (4); and wherein the light guide module comprises a rotatable lens holder (11), the rotatable lens holder (11) is fixedly provided with a linear Fresnel lens (12) on an upper end thereof, the rotatable lens holder (11) is provided with a light guide plate (13) on a lower end thereof, one side of the linear Fresnel lens (12) is provided with a step motor (10), and the step motor (10) is arranged on the fixing frame (6); and wherein the number of the rotary members is two or more, the linear Fresnel lens (12) is driven by the step motor (10) to slowly rotate with a change of angle of sunlight, so that the sunlight is always linearly focused on one side of the light guide plate (13) to form an area light source on two sides of the light guide plate (13), the linear Fresnel lens (12) is arranged on a top end of two adjacent rotary members, the light guide plate (13) is inserted between adjacent rotary members and the light guide plate (13) is parallel to a surface of the algae biofilm growth carrier (2), the low-speed motor (1) is connected to the driving shaft (3) and rotated, and the power transmission belt (9) drives the driven shaft (4) submerged under the liquid surface of the reaction tank (5) to rotate, so that the algae biofilm growth carrier (2) is rotated alternately in the gas-liquid medium in the reaction tank (5) following the power transmission belt (9).

2. The compact rotary algae biofilm reactor according to claim 1, wherein the rotatable lens holder (11) has a base in an inverted V shape.

3. The compact rotary algae biofilm reactor according to claim 1, wherein the algae biofilm growth carrier (2) is a flexible material.

4. The compact rotary algae biofilm reactor according to claim 3, wherein the flexible material is a silicone film, nylon cloth, a cotton and linen product or a flexible plastic.

5. The compact rotary algae biofilm reactor according to claim 1, wherein a water inlet (8) is provided at a bottom of one side of the reaction tank (5), and a water outlet (7) is provided on another side opposite the water inlet (8).

6. The compact rotary algae biofilm reactor according to claim 1 wherein the light guide plate illuminates the algae biofilm growth carrier of each adjacent rotary member in air above the liquid surface of the reaction tank.

7. The compact rotary algae biofilm reactor according to claim 6 wherein the light guide plate extends over substantially an entire height of each adjacent rotary member above the reaction tank.

8. A compact rotary algae biofilm reactor comprising:
a reaction tank for containing a liquid to be treated;
a fixing frame disposed atop the reaction tank;
a plurality of rotary members, each rotary member comprising a driving shaft which has a lengthwise direction and is rotatably supported on the fixing frame above the reaction tank, a driven shaft rotatably mounted inside the reaction tank at a height at which it can be submerged within the reaction tank, a first motor disposed on an upper portion of the fixing frame and drivingly connected to the driving shaft for rotating the driving shaft, a power transmission belt connecting the driving shaft and the driven shaft for transmitting rotation of the driving shaft to the driven shaft, and an algae biofilm growth carrier wound around the driving shaft and the driven shaft such that the algae biofilm growth carrier travels in a continuous path around the driving shaft and the driven shaft when the first motor rotates the driving shaft;
at least one light guide module, each light guide module comprising a light guide plate disposed between two adjacent ones of the rotary members and having first and second light emitting surfaces each opposing one of the algae biofilm growth carriers of the adjacent rotary members in air above the reaction tank for illuminating portions of the algae biofilm growth carriers outside of the reaction tank, a linear Fresnel lens which is disposed above the fixing frame and has a focal point coinciding with an upper end of the light guide plate when the lens is irradiated with light perpendicular to a plane of the Fresnel lens and focuses light into a linear light band extending in the lengthwise direction of the driving shaft and is supported for movement along an arc centered on the focal point, and a second motor drivingly connected to the Fresnel lens for moving the Fresnel lens along the arc.

9. The compact rotary algae biofilm reactor according to claim 8 wherein each light guide plate is parallel to the algae biofilm growth carriers of the adjacent rotary members.

10. The compact rotary algae biofilm reactor according to claim 8 wherein each light guide plate is vertical.

11. The compact rotary algae biofilm reactor according to claim 8 wherein each light guide plate irradiates portions of the carriers located outside the reaction tank.

12. The compact rotary algae biofilm reactor according to claim 8 wherein the second motor comprises a step motor.

13. The compact rotary algae biofilm reactor according to claim 8 wherein each light guide module includes a rotatable lens holder on which the Fresnel lens is mounted, and which is drivingly connected to the second motor for rotation about an axis offset from the Fresnel lens.

14. The compact rotary algae biofilm reactor according to claim 8 wherein the reaction tank contains a liquid for treatment which contains no activated sludge, and each driven roller is submerged in the liquid.

15. The compact rotary algae biofilm reactor according to claim 8 wherein each Fresnel lens is disposed above upper ends of the adjacent rotary members and overlaps the adjacent rotary members in a horizontal direction.

16. The compact rotary algae biofilm reactor according to claim 8 wherein for each rotary member, the driving shaft is coaxially connected to the first motor.

\* \* \* \* \*